(12) United States Patent
Baikoff

(10) Patent No.: US 6,692,524 B2
(45) Date of Patent: Feb. 17, 2004

(54) TECHNIQUES AND IMPLANTS FOR CORRECTING PRESBYOPIA

(76) Inventor: Georges Baikoff, 317, Corniche Kennedy, F-13007 Marseille (FR)

(*) Notice: Subject to any disclaimer, the term of this patent is extended or adjusted under 35 U.S.C. 154(b) by 0 days.

(21) Appl. No.: 10/235,884

(22) Filed: Sep. 6, 2002

(65) Prior Publication Data
US 2003/0060748 A1 Mar. 27, 2003

Related U.S. Application Data

(63) Continuation-in-part of application No. 10/129,457, filed as application No. PCT/FR02/00179 on Jan. 17, 2002.

(30) Foreign Application Priority Data
Jan. 19, 2001 (FR) .............................. 01 00703

(51) Int. Cl.⁷ .................................................. A61F 2/14
(52) U.S. Cl. ...................................................... 623/4.1
(58) Field of Search ................................ 623/4.1, 6.64, 623/905, 5.14

(56) References Cited

U.S. PATENT DOCUMENTS 6,007,578 A * 12/1999 Schachar .................. 623/11.11
6,280,468 B1 * 8/2001 Schachar .................... 623/4.1
6,299,640 B1 * 10/2001 Schachar .................... 623/4.1
6,358,279 B1 * 3/2002 Tahi et al. ................... 623/4.1
6,494,910 B1 * 12/2002 Ganem et al. ............... 623/4.1
6,517,555 B1 * 2/2003 Caro ........................... 606/151
6,579,316 B2 * 6/2003 Schachar .................... 623/4.1
2002/0035397 A1 * 3/2002 Baikoff ........................ 623/4.1
2002/0161433 A1 * 10/2002 Baikoff et al. ............... 623/4.1

FOREIGN PATENT DOCUMENTS

FR   2 784 287        4/2000
FR   2 787 991        7/2000
WO   WO 00/74600 A1 * 12/2000 ................. 624/4.1

* cited by examiner

Primary Examiner—David H. Willse
Assistant Examiner—Suzette J. Jackson
(74) Attorney, Agent, or Firm—Young & Thompson

(57) ABSTRACT

Presbyopia is more effectively corrected by techniques and implants designed to exert an inwardly-directed force on the ciliary body. The force is preferably either perpendicular to the optical axis, or generally perpendicular wherein the zonular plexus is deflected inwardly approximately along an axis bisecting the angle described by the anterior zonular fibers when viewed in a horizontal plane.

11 Claims, 3 Drawing Sheets

TECHNIQUES AND IMPLANTS FOR CORRECTING PRESBYOPIA

This application is a continuation-in-part of my co-pending application Ser. No. 10/129,457, filed Jul. 12, 2002 which is the U.S. national phase of International Application PCT/FR02/00179 filed Jan. 17, 2002, which in turn claims priority of French application no. 0100703 filed in France on Jan. 19, 2001.

BACKGROUND OF THE INVENTION

1. Field of the Invention

The present invention relates generally to the correction of vision by insertion of a corrective element into the eye, and more precisely the correction of presbyopia.

2. Description of Related Art

It will be recalled that, as shown in FIG. 1, the lens Cr enclosed in the lens sac S is suspended from the ciliary body Cc by means of the zonule Z. This ciliary body Cc lines the internal surface of the sclera about a ring located on the average at a latitude distant by 2 to 3 mm from the limbus, measured along the optical axis.

Presbyopia is a loss or reduction of the accommodating power of the eye which takes place when the person ages.

According to a theory of about a hundred years ago, Von Helmholtz explained the physiology of the accommodation of near vision by a relaxation of the zonule tension exerted on the lens during contraction of the ciliary body. This relaxation of tension gives rise to the lens taking a more globular form having smaller radii of curvature and hence more convergent as to the focal point. At the same time, the lens moves forward in an antero-posterior plane.

Schachar proposed beginning in 1992, particularly in his U.S. Pat. Nos. 5,354,331, 5,465,737, 5,489,299 and 6,007,578, a theory contrary to that of Von Helmholtz, according to which the accommodation was due to a tensile force exerted on the lens when the ciliary body relaxes, such a force tensioning the zonule ligament which creates a flattening of the periphery of the lens and a convex projection of the center of the latter.

Moreover, according to Schachar, the diameter of the lens increases in the course of aging and the distance separating the periphery of the lens from the ciliary body diminishes bit by bit, which leads to a relaxation of the zonule. As a result, the centrifugal effort exerted by the ciliary body on the periphery of the lens is no longer sufficiently great to ensure the accommodation.

Schachar proposed in the patents mentioned above, different methods permitting improving the accommodation power of an eye, consisting for example in surgically reducing the length of the zonules or the diameter of the lens, or preventing enlargement of the lens.

Another method of treatment proposed by Schachar has been very widely used. It consists in treating presbyopia by positioning a truncated conical ring about the scleral ring to create a sort of external suspension, so as to enlarge the diameter of the ciliary body and hence to restretch the zonule.

Such an intervention being fairly important, it has been proposed subsequently to position on the sclera arcuate scleral expansion segments, of a radius of curvature less than the radius of curvature of the sclera. These segments pass through passages encised in the surface of the sclera concentrically to the limbus, in line with the ciliary body, and bear with their ends on the external surface of the sclera.

In FR 98 12834 of the applicant, such segments have ends of spatulate form so as not to risk perforating the sclera at the points of bearing of the segment on the sclera and preventing turning of said segments.

It has been noted that the operations carried out since 1992 by following the Schachar theory have sometimes succeeded and permitted giving the patient good vision, but sometimes not, the accommodation not being really better after the intervention.

Moreover, in certain patients, the segments have been expelled from the sclera, after pulling out of the passages in which they were positioned.

As a result, the Schachar theory is not able to solve the problem of the treatment of presbyopia.

SUMMARY OF THE INVENTION

By analyzing the results of procedures practiced by specialists, the applicant has arrived at the conclusion that the Schachar theory was inexact even though its practice permitted in certain cases obtaining the desired result.

The applicant concluded that the correction of presbyopia observed in certain patients after implantation of a truncated conical ring or arcuate segments on the sclera would not do as Schachar thought, to an effect of traction exerted on the zonule and hence on the lens, but to an induced result obtained during the procedure without the operator seeking it.

The applicant has taken account of the fact that the eyeball has a flexible but inextensible surface and has concluded that it is not possible to increase the circumference of the scleral ring by exerting centrifugal tension at certain points on the sclera.

By examining in greater detail the procedures carried out according to the Schachar method, the applicant has determined that by exerting a centrifugal tension at certain points, the emplacement of segments of scleral expansion would exert as a reaction a centripetal pressure in line with their points of bearing on the sclera.

The applicant thus explains the observed effect with certain rings or scleral expansion segments, not by the traction that they exert on the zonule at certain points, but by the pressure that they exert on the latter at other points. When the pressure is exerted in line with the ciliary body, it artificially compensates the defect of contraction of said ciliary body and helps the eye in its accommodation work as was described by Von Helmholtz.

These observations led the applicant to provide by the present invention techniques and corrective elements permitting correcting presbyopia reproducibly and not at random, as in the procedures proposed for about the last ten years.

To this end, the invention relates to techniques and novel corrective element permitting correcting presbyopia, adapted to be implanted in the eye adjacent the ciliary body, characterized in that the corrective elements are shaped to exert on said ciliary body a centripetal force directed perpendicularly to the optical axis.

This element is noteworthy in that it has, in cross-section, an external wall adapted to be disposed parallel to the surface of the sclera and an internal wall adapted to be disposed parallel to the optical axis of the eye.

The sclera being inextensible, such an element acts by bearing on the portion of the sclera which it covers to press the ciliary body in the direction of the optical axis of the eye and to form indentations in said ciliary body. As a result, centripetal forces on said ciliary body artificially compensate the loss of contraction of the latter and thus re-establish its action necessary for accommodation, which is to say the zonular relaxation.

The increase of the contractive force of the ciliary body with a decrease of the diameter of the ciliary ring by elements forming indentations in the ciliary body, permits relaxing the zonule and letting the lens profit from its residual flexibility to become more globular.

The corrective element according to the invention is all the more remarkable in that, in one embodiment:

it is constituted by an arcuate segment whose radius of curvature is such that after its emplacement in the eye, said segment will be centered on the optical axis of said eye, a rear wall connects the rear elongated ends to each other of said external and internal walls, a rounded portion connects the concurrent front ends of said external and internal walls, the angle comprised between the external wall and the internal wall is of the order of 45°, the rear wall is rounded, the rear wall is constituted by a portion of a torus.

In further refinement of the present invention, it has been recognized that an even more enhanced and enduring correction of presbyopia will be achieved by shaping and positioning the corrective element such that it exerts a force approximately at the zonular plexus, which is directed interiorly of the eye and along an axis that approximately bisects the angle described by the anterior zonular fiber system when viewed in a horizontal plane.

Therefore, a wide variety of shapes and sizes of the corrective element according to the invention are possible in addition to that described above, provided that the shape and location and orientation of implantation are selected to produce an interiorly directed force that most effectively relaxes the anterior zonular fiber system.

BRIEF DESCRIPTION OF THE DRAWINGS

The invention will be better understood from the description which follows given by way of non-limiting example and with reference to the accompanying drawings, in which.

DETAILED DESCRIPTION OF PREFERRED EMBODIMENTS

Figure 1:
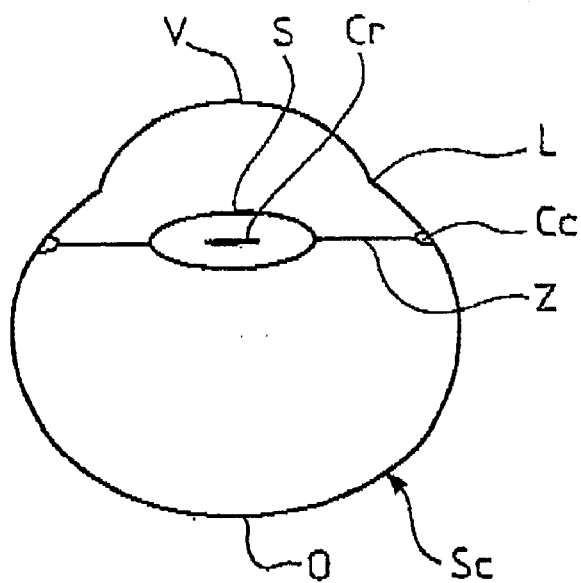
FIG. 1 is a schematic view in cross-section of an eye.
Figure 2:
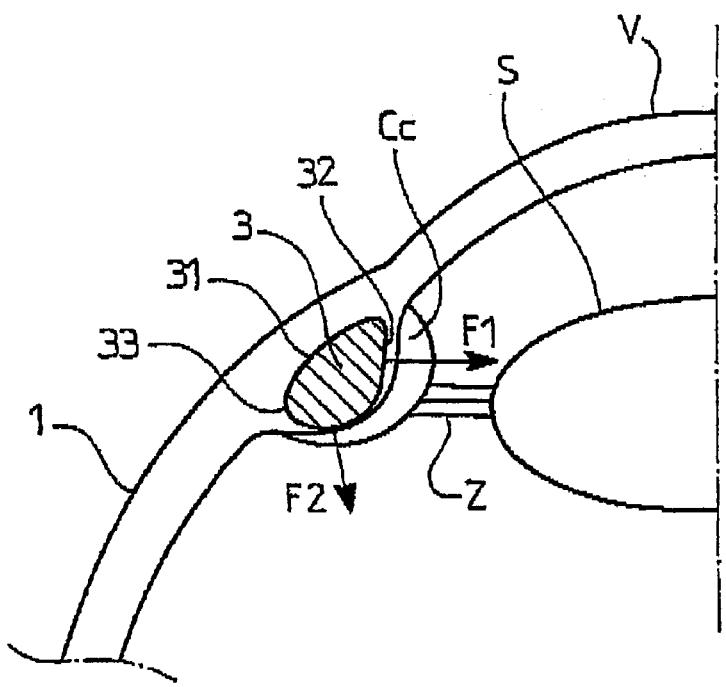
FIG. 2 is a fragmentary cross-sectional view of an eye in which is implanted a corrective element according to the invention.

In FIG. 2, there is schematically shown at 1 the surface of the sclera in line with the ciliary body and at 2 the optical axis of the eye.

The terms front and rear, sometimes also referred to as anterior and posterior, respectively, are defined relative to the eye.

Figure 3:
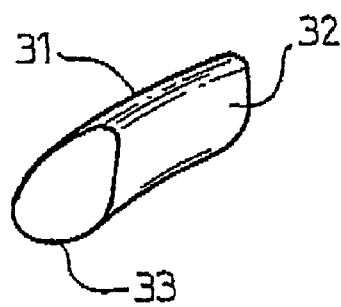
FIG. 3 is a perspective view of a corrective element according to the invention.

FIGS. 2 and 3 show an element 3 according to one preferred embodiment of the invention. This element is constituted by an arcuate segment whose radius of curvature is such that it will be centered on the optical axis 2 of the eye when it is in place, and hence such that said segment will be parallel to the scleral ring at the level of the insertion of the ciliary muscle. Said arcuate segment has for example a length of the order of 4 to 5 millimeters and a radius of curvature of the order of 7 millimeters.

As seen in cross-section, the element 3 overall has the shape of a triangle. It comprises an external wall 31 adapted to be disposed parallel to the surface 1 of the sclera, an internal wall 32 adapted to be disposed parallel to the optical axis 2 of the eye.

Given the geometry of the eye, this external wall 31 and internal wall 32 of the element 3 define between them an angle of about 45°.

Said external wall 31 and internal wall 32 have concurrent ends toward the front of the element 3 and spaced from each other rearwardly.

A rear wall 33 connects the rear spaced ends of the external wall 31 and internal wall 32 and a rounded portion connects the front concurrent ends of the two walls.

In a manner known per se, the sclera is a semi-rigid and inextensible body whilst the ciliary body is a soft tissue. A foreign body introduced between the sclera and the ciliary body thus cannot deform the sclera but gives rise to a deformation of the ciliary body. As a result, when it is emplaced in the eye, in line with the ciliary body, the element 3 bears with its external wall 31 on the inextensible portion of the sclera which covers it to exert on the ciliary body Cc a centripetal force F1 oriented perpendicularly to the internal wall 32, hence perpendicularly to the optical axis 2, and directed toward said optical axis 2. Such a force acts directly on the ciliary body Cc and exerts on the latter a pressure which presses it back in the direction of the optical axis 2 of the eye, which artificially creates a displacement of the latter similar to that which takes place during contraction of said ciliary body. This displacement has the effect of relaxing the zonule Z, along the axis of this latter. This effect compensates the loss of contraction power of the ciliary body and permits the lens to take a more globular shape having smaller radii of curvature.

The front end of the element 3 is preferably rounded so as to avoid harming the tissues of the eye.

The rear wall 33 can be more or less rounded.

Preferably, said rear wall 33 is so arranged as to give to the cross-section of the corrective element 3 a shape similar to a drop, to this end it can be constituted by a toric portion. Such a construction permits further improving the correction arising from the corrective element 3 by supplying a pressure force F2 exerted on the ciliary body Cc by the rear wall 33.

The force F2 is oriented toward the center and toward the rear of the eye, and ensures a compression of the vitreous humor and induces a pressure, and hence a movement, of the lens forwardly similar to that described by Von Helmholtz.

The corrective element 3 according to the invention is disposed at the deep surface of the scleral plane to take best advantage of the forces due to the inextensibility of the sclera and near the surface of the soft body constituted by the ciliary body, through insertions of small dimensions provided in the sclera, or between the sclera and the ciliary body as shown in the drawing.

So as to obtain a maximum effect, the emplacement of the element according to the invention must be carried out by making an incision in the sclera to a depth of at least 600 microns and providing at this depth a blind tunnel extending parallel to the surface of the sclera. Echography can be used before the operation to verify the thickness of the sclera so as not to risk injuring the ciliary body. After insertion of the corrective element, the incision is sutured so that the element remains positioned deep in the sclera.

To treat presbyopia, several elements are distributed in the eye, about the ciliary body, so as to constitute several pressure zones distributed about the lens and to induce in the latter effects similar to that which it undergoes during contraction of a young ciliary body. There will be positioned for example 3 to 8 segments according to the invention in the eye of the patient, preferably 4 segments disposed at 90° from each other.

The corrective element 3 is preferably provided so as to have in cross-section a length parallel to the optical axis such that it will bear against the ciliary body even it is not perfectly well positioned in line with the latter. To this end, the length of the internal wall 32 is for example of the order of 0.5 to 0.7 millimeter.

The length of the external wall 31 is for example of the order of 0.7 to 1 millimeter, and the thickness of the segment 3, defined perpendicular to said internal wall 32, is for example of the order of 0.5 to 0.7 millimeter.

According to an alternative embodiment not shown in the drawing, the corrective element 3 according to the invention is constituted by a cylindrical ring disposed within the sclera, about the ciliary body.

According to still another embodiment not shown in the drawing, the corrective element is not of uniform cross-section over all its length. It can have regions with a triangular cross-section acting on the ciliary body and regions with a smaller cross-section that have no or little action on the ciliary body. Such an embodiment permits creating a large number of points of bearing on the ciliary body so as better to distribute the forces exerted on the latter.

Figure 4:
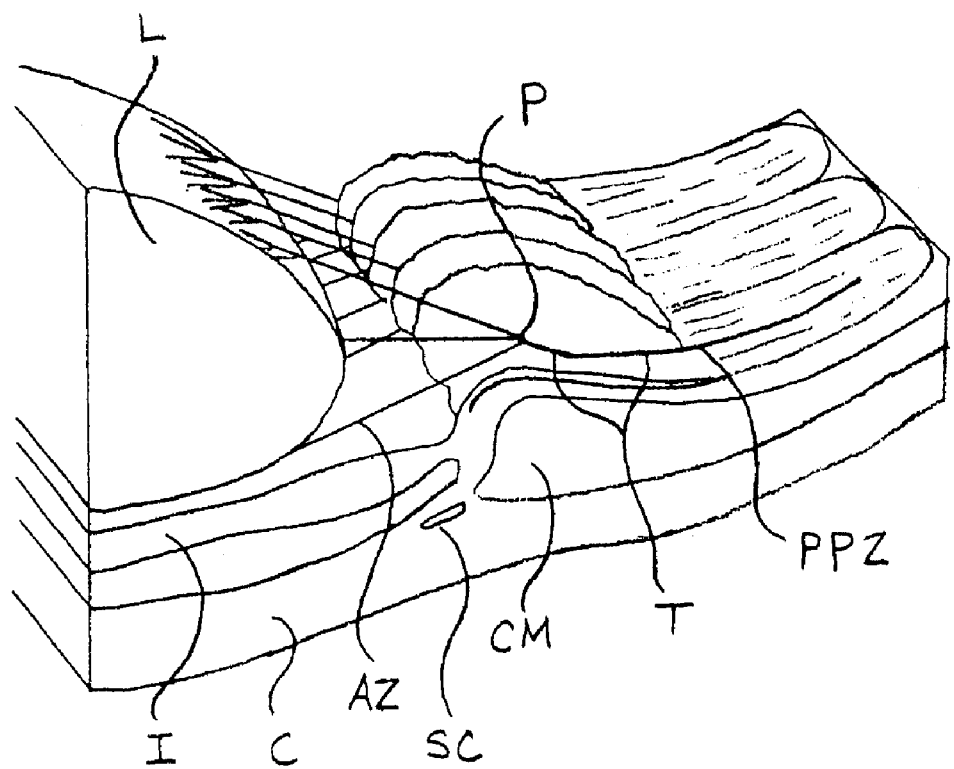
FIG. 4 is a schematic perspective view that shows in somewhat greater detail the anterior zonular fiber system.

In FIG. 4, the anterior zonular apparatus is depicted in somewhat greater detail. The lens L is suspended in its sac or capsule via the anterior zonules AZ, which converge at the zonular plexus P (sometimes also called the zonular fork). Posteriorly of the zonular plexus P, the posterior zonular fibers PPZ extend as suspensory ligament in the area of the pars plana, wherein T designates the tension fiber system in the area of the ciliary valleys. Also denoted in FIG. 4 are the iris I, cornea C, Schlemm canal SC and ciliary muscle CM.

At the zonular plexus P, the zonular apparatus is connected to the ciliary process or the ciliary valleys via the tension fiber system T, and is therefore fixed to the ciliary body.

Figure 5:
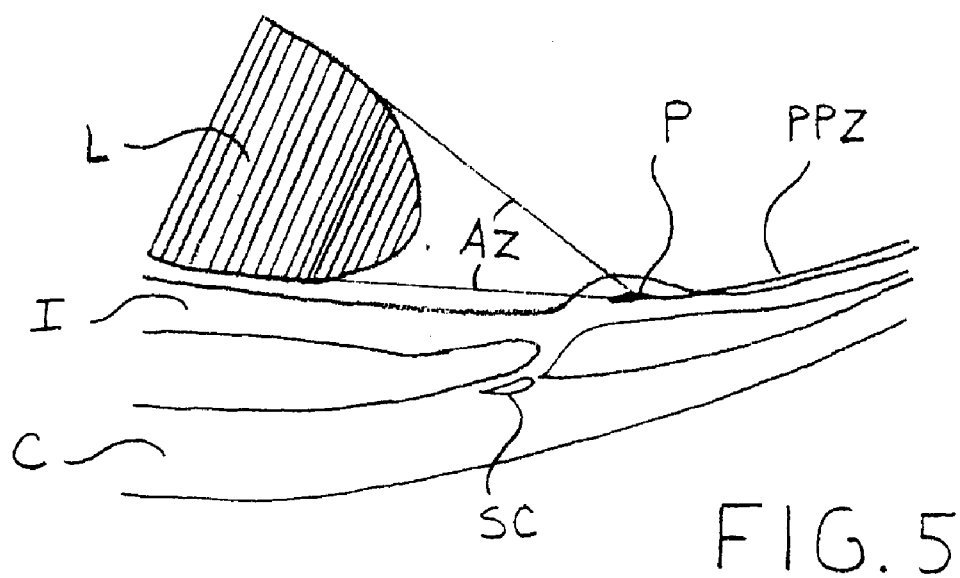
FIG. 5 is a schematic view in cross-section illustrating the angular range described by the anterior zonules when viewed in a horizontal plane.

As is shown more clearly in FIG. 5, the anterior zonules, when viewed in a horizontal plane, are arrayed over an angular range describing an acute angle, as depicted in the figure.

Figure 6:
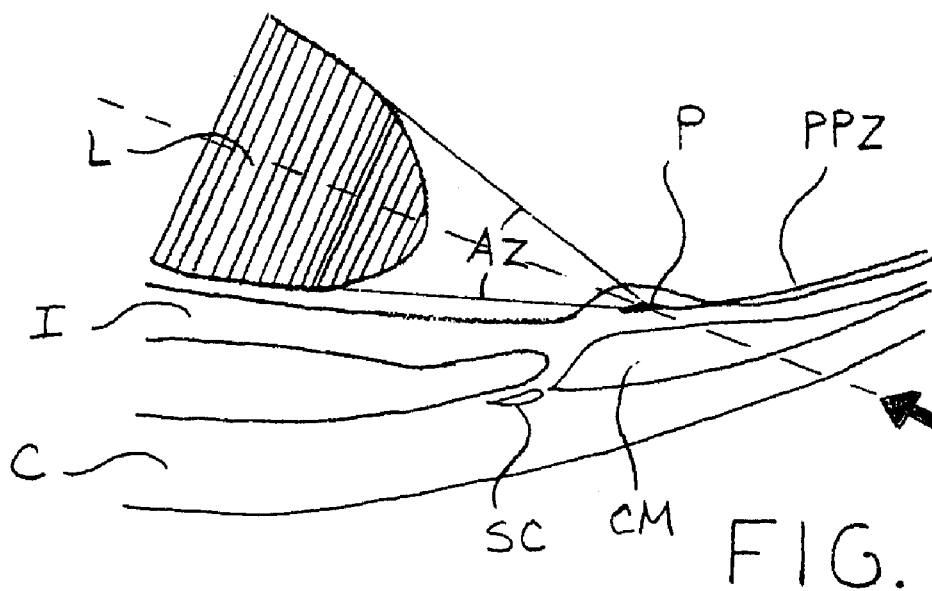
FIG. 6 is a view similar to FIG. 5, showing a preferred direction and orientation of the force applied by the corrective elements according to the invention, when implanted by the techniques according to the invention.

An important further improvement in correcting presbyopia is achieved if the corrective element is designed and surgically implanted such that an inwardly directed force is generated along an axis that bisects the AZ angle depicted in FIG. 5. The direction and orientation of this force axis is shown in FIG. 6. It is believed that a force so directed and so oriented causes a relaxation of the zonules that is more evenly distributed over the anterior zonular apparatus as a whole, and thus more effectively and enduringly corrects presbyopia.

The bisecting axis depicted in FIG. 6 extends approximately from the zonular plexus P to the equator of the crystalline lens. The bisecting axis extends generally perpendicular to the optical axis of the eye; however, in this case, the bisecting axis centrally of the eye is disposed more toward the back of the eye along the optical axis than it is in the vicinity of the zonular plexus P. Hence the bisecting axis has a major component perpendicular to the optical axis and a distinctly minor component parallel to the optical axis.

Figure 7:
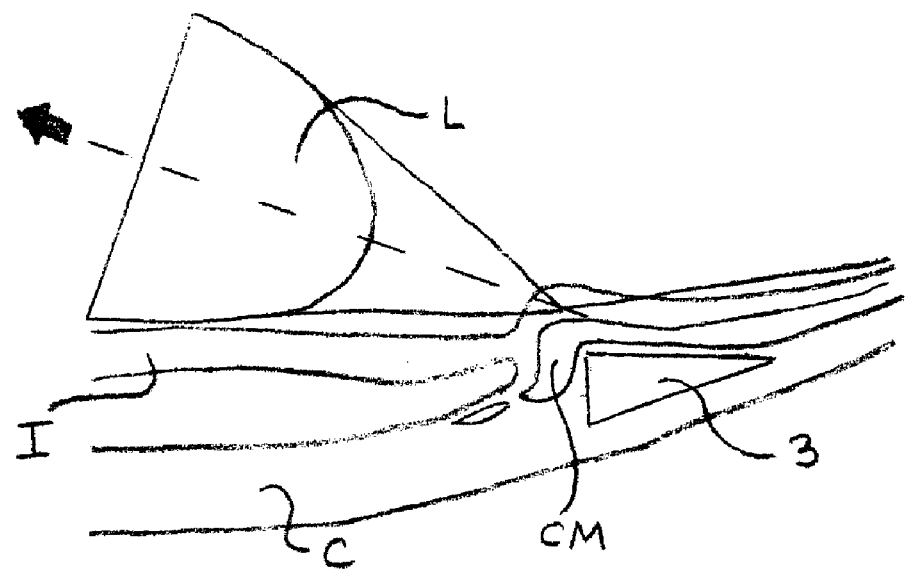
FIG. 7 is a view similar to FIG. 5, but showing a corrective element implanted according to the techniques of the invention, to exert the corrective force depicted in FIG. 6.

FIG. 7 depicts a corrective element that is shaped and oriented so as to exert the desired force along the bisecting axis. The shape of the element in the embodiment of FIG. 7 is depicted as being generally triangular, as in the embodiment of FIGS. 2 and 3. In this case, however, it will be appreciated that the shape of the element as well as its orientation have been altered in relation to FIG. 2, so as more precisely to mimic the accommodating action of the ciliary body in a patient not afflicted with presbyopia, i.e., an inward deflection of the zonular plexus P along the indicated bisecting axis.

The corrective element is otherwise generally as described in connection with the embodiment of FIGS. 2 and 3, for example as regards its overall dimensions and annular shape. It is furthermore implanted in the same manner, by cutting a deep blind tunnel in the sclera, preferably to a depth of at least about 600 microns, bearing in mind that the thickness of the sclera in this region is approximately 800 microns. After implantation, the tunnel is closed with a suture. The deeper that the corrective element is implanted within the sclera, and the more securely it is retained there, the less the chance that the corrective element will subsequently be expelled with an attendant loss of the corrective effect.

Also in this embodiment, anywhere from three to eight or more of these corrective elements are preferably implanted, distributed about the circle described by the ciliary body.

The recognition by the present inventor of the particular force mechanism that is optimum for addressing and correcting the physiology of presbyopia opens up a wide variety of suitable shapes for the corrective implant, which are effective to achieve that result. Therefore, in addition to a generally triangular cross-section for the implant, it is possible, without limitation, to form corrective elements (implants) whose cross-section is e.g. rectangular, circular, oval, regular polygonal and irregular polygonal. Common to all such embodiments is that the implant is shaped such that its inwardly directed surface, in the implanted state, causes a deflection of the zonular plexus P inwardly along the bisecting axis, as shown in FIGS. 6 and 7.

Consistent with the description of the first embodiment, it will be understood that the reference in the preceding paragraph to a variety of geometrical shapes as possible cross-sectional configurations for the novel implant does not exclude, and preferably includes, shapes wherein the sides are joined by rounded surfaces.

Also, while the designated bisecting axis represents the direction of deflection regarded as optimum, in practice the surgically implanted corrective elements may exert inwardly directed forces that deviate from the ideal bisecting axis to some extent. Deviations of up to ±25% of the overall angular range AZ are possible, although deviations of ±10% or less are preferred.

Although the present invention has been described in connection with various preferred embodiments thereof, it will be understood by those skilled in this art that those embodiments are described solely for purposes of illustrating the present invention, and should in no way be construed in a limiting sense. Instead, various modifications and substitutions of equivalent techniques will be readily apparent to those skilled in this art after reading the foregoing specification, and all such modifications and substitutions are to be understood as falling within the true scope and spirit of the appended claims.

What is claimed is:

1. A method for correcting presbyopia, comprising implanting in the sclera of a patient at least one corrective element shaped and positioned so as to exert an inwardly directed force on the zonular plexus approximately along an axis bisecting the angle described by the anterior zonular fibers when viewed in a horizontal plane.

2. The method according to claim 1, wherein said at least one corrective element is implanted by forming a blind tunnel in the sclera at a depth of at least about 600 microns.

3. The method according to claim 1, wherein said implanting step comprises implanting from three to eight corrective element are implanted in a circular array about the ciliary body.

4. The method according to claim 1, wherein said inwardly directed force is oriented within 25% of said axis in relation to said angle.

5. The method according to claim 1, wherein said inwardly directed force is oriented within 10% of said axis in relation to said angle.

6. The method according to claim 2, wherein said blind tunnel is sutured after implanting said at least one corrective element.

7. Element for correcting presbyopia, comprising a body shaped such that, when implanted in the sclera of a patient adjacent the zonular plexus, it exerts an inwardly directed force on the zonular plexus approximately along an axis bisecting the angle described by the anterior zonular fibers when viewed in a horizontal plane.

8. The element according to claim 7, wherein said body is generally triangular in cross-section.

9. The element according to claim 7, wherein said body comprises an external wall adapted to be disposed parallel to the surface of the sclera an internal projection deflecting the zonular plexus along said axis.

10. The element according to claim 7, wherein said body is generally circular, oval, or polygonal in cross-section.

11. The element according to claim 7, wherein said body is an arcuate segment whose radius of curvature is such that after its emplacement in the eye, said segment will be centered on the optical axis of said eye.

* * * * *

(12) EX PARTE REEXAMINATION CERTIFICATE (6091st)
United States Patent
Baikoff

(10) Number: US 6,692,524 C1
(45) Certificate Issued: Jan. 8, 2008

(54) TECHNIQUES AND IMPLANTS FOR CORRECTING PRESBYOPIA

(75) Inventor: Georges Baikoff, Marseilles (FR)

(73) Assignee: Opthalmic Lenders, LLC, Dallas, TX (US)

Reexamination Request:
No. 90/008,186, Aug. 25, 2006

Reexamination Certificate for:
Patent No.: 6,692,524
Issued: Feb. 17, 2004
Appl. No.: 10/235,884
Filed: Sep. 6, 2002

Related U.S. Application Data

(63) Continuation-in-part of application No. 10/129,457, filed as application No. PCT/FR02/00179 on Jan. 17, 2002, now Pat. No. 6,682,560.

(30) Foreign Application Priority Data

Jan. 19, 2001 (FR) .............................. 01 00703

(51) Int. Cl.
*A61F 2/14* (2006.01)

(52) U.S. Cl. ......................................... 623/4.1
(58) Field of Classification Search ...................... None
See application file for complete search history.

(56) References Cited

U.S. PATENT DOCUMENTS

| | | | |
|---|---|---|---|
| 6,007,578 A | 12/1999 | Schachar | 623/4 |
| 6,197,056 B1 | 3/2001 | Schachar | 623/4.1 |
| 6,280,468 B1 | 8/2001 | Schachar | 623/4.1 |
| 6,712,847 B2 | 3/2004 | Bakoff et al. | 623/4.1 |

*Primary Examiner*—Jeffrey R. Jastrzab

(57) ABSTRACT

Presbyopia is more effectively corrected by techniques and implants designed to exert an inwardly-directed force on the ciliary body. The force is preferably either perpendicular to the optical axis, or generally perpendicular wherein the zonular plexus is deflected inwardly approximately along an axis bisecting the angle described by the anterior zonular fibers when viewed in a horizontal plane.

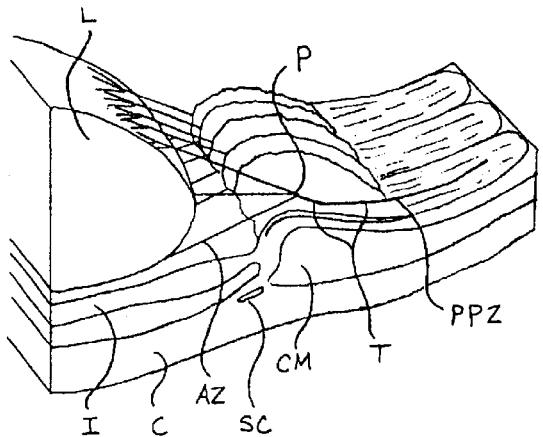

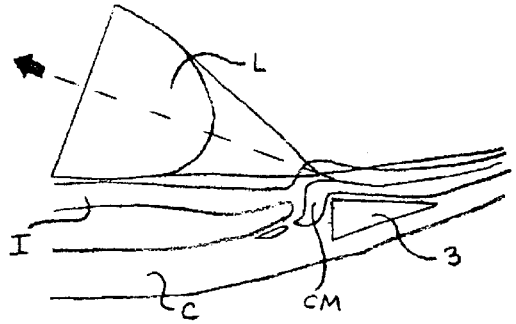

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–11 is confirmed.

New claims 12 and 13 are added and determined to be patentable.

*12. The method according to claim 1, wherein the corrective element is implanted so as to form an indentation in the ciliary body.*

*13. The element according to claim 7, wherein said body, when implanted in the sclera of a patient adjacent the zonular plexus, forms an indentation in the ciliary body.*

\* \* \* \* \*